United States Patent
Jackson

(10) Patent No.: US 9,776,317 B1
(45) Date of Patent: Oct. 3, 2017

(54) CONTOUR-ADJUSTABLE TOOTHBRUSH

(71) Applicant: Steve Jackson, Modesto, CA (US)

(72) Inventor: Steve Jackson, Modesto, CA (US)

( * ) Notice: Subject to any disclaimer, the term of this patent is extended or adjusted under 35 U.S.C. 154(b) by 0 days.

(21) Appl. No.: 15/146,177

(22) Filed: May 4, 2016

(51) Int. Cl.
*A61C 17/34* (2006.01)
*B25G 1/02* (2006.01)
*A46B 9/04* (2006.01)
*A46B 9/02* (2006.01)
*B25G 1/10* (2006.01)
*A46B 13/02* (2006.01)
*B25G 1/06* (2006.01)
*A61C 17/22* (2006.01)
*A46B 9/06* (2006.01)

(52) U.S. Cl.
CPC ............... *B25G 1/02* (2013.01); *A46B 9/025* (2013.01); *A46B 9/04* (2013.01); *A46B 9/045* (2013.01); *A46B 13/02* (2013.01); *A61C 17/222* (2013.01); *A61C 17/225* (2013.01); *A61C 17/34* (2013.01); *A61C 17/3481* (2013.01); *B25G 1/06* (2013.01); *B25G 1/102* (2013.01); *A46B 9/06* (2013.01); *A46B 2200/1066* (2013.01)

(58) Field of Classification Search
CPC .. A46B 13/02; A46B 5/02; A46B 9/04; A61C 17/34; A61C 17/3481; A61C 17/222; A61C 17/225
USPC ...................................... 15/22.1, 22.2, 167.1
See application file for complete search history.

(56) References Cited

U.S. PATENT DOCUMENTS

| | | | | |
|---|---|---|---|---|
| 1,565,750 A | * | 12/1925 | Nathanson | A46B 5/0012 15/167.1 |
| 1,709,262 A | * | 4/1929 | Henderhan | A46B 5/0012 15/167.2 |
| 3,592,188 A | * | 7/1971 | Barnett | A61C 17/40 15/22.1 |
| 5,137,039 A | * | 8/1992 | Klinkhammer | A46B 5/0091 132/308 |
| 5,148,567 A | * | 9/1992 | Daub | A46B 7/04 15/167.2 |
| 5,171,066 A | * | 12/1992 | Klinkhammer | A46B 5/002 300/21 |
| 5,177,826 A | * | 1/1993 | Vrignaud | A61C 17/24 15/22.1 |
| 5,305,491 A | * | 4/1994 | Hegemann | A46B 5/0012 15/167.2 |
| 5,497,526 A | * | 3/1996 | Klinkhammer | A46B 5/0012 132/309 |

(Continued)

*Primary Examiner* — Michael Jennings

(57) ABSTRACT

A contour-adjustable toothbrush is a device that provides a more thorough brushing experience while eliminating the need to remove the device from the mouth during brushing. A first brushing assembly and a second brushing assembly are slidably engaged into a housing handle that may be grasped by the user. The first brushing assembly and the second brushing assembly each include a flexible brush head with a concave surface. The concave surface of the first brushing assembly is oriented away from the concave surface of the second brushing assembly, enabling the first brushing assembly and the second brushing assembly to clean the upper teeth and lower teeth simultaneously. The first brushing assembly and the second brushing assembly are independently adjustable in order to adjust the length of the device. An electronic variant of the device includes a power supply and at least one actuator.

10 Claims, 11 Drawing Sheets

(56) References Cited

U.S. PATENT DOCUMENTS

| | | | | |
|---|---|---|---|---|
| 5,791,007 | A * | 8/1998 | Tsai | A46B 5/0012 15/167.1 |
| 5,842,244 | A * | 12/1998 | Hilfinger | A61C 17/22 15/22.1 |
| 5,934,762 | A * | 8/1999 | Vrignaud | A46B 5/0012 15/106 |
| 6,138,689 | A * | 10/2000 | Stern | A46B 5/0012 132/309 |
| 6,381,794 | B1 * | 5/2002 | Porper | A46B 5/0012 15/167.2 |
| 8,887,338 | B1 * | 11/2014 | Brar | A46B 5/0012 15/167.1 |
| 9,198,505 | B1 * | 12/2015 | Brar | A46B 5/0012 |
| 2002/0152563 | A1 * | 10/2002 | Sato | A46B 9/026 15/22.1 |
| 2006/0059638 | A1 * | 3/2006 | Hegemann | A61C 1/0092 15/22.2 |
| 2008/0010770 | A1 * | 1/2008 | Hegemann | A46B 5/0012 15/167.1 |
| 2008/0083075 | A1 * | 4/2008 | Dickie | A46B 9/045 15/22.2 |
| 2008/0230246 | A1 * | 9/2008 | Dollar-Wright | A45D 24/007 173/29 |
| 2011/0314622 | A1 * | 12/2011 | Hong | A46B 5/0025 15/167.1 |
| 2014/0137350 | A1 * | 5/2014 | Wen | A46B 5/023 15/143.1 |
| 2014/0283319 | A1 * | 9/2014 | Truocchio | A46B 5/02 15/145 |
| 2014/0317864 | A1 * | 10/2014 | Walther | A46B 17/02 15/143.1 |
| 2015/0342332 | A1 * | 12/2015 | Walther | A46B 5/02 15/143.1 |

* cited by examiner

DETAIL A

DETAIL B

DETAIL C

US 9,776,317 B1

CONTOUR-ADJUSTABLE TOOTHBRUSH

FIELD OF THE INVENTION

The present invention relates generally to a toothbrush. More specifically, the present invention is a contour-adjustable toothbrush that conforms to the contour of the user's teeth. The present invention does not need to be removed from the user's teeth during the brushing and provides a more thorough brushing experience.

BACKGROUND OF THE INVENTION

Learning proper brushing technique is essential for long-term dental health and hygiene. This is particularly the case with children as it is important that good dental habits are acquired early and carried on to later life. There are several difficulties and obstacles that children must overcome when first learning proper brushing technique. One potential difficulty is the potential of gagging and impalement due to the presence of the toothbrush in the mouth to which a child is unaccustomed. While toothbrushes that are sized for children do exist, these toothbrushes may still be potentially too large for comfortable use when brushing. A potential consequence of learning improper brushing technique is the failure to thoroughly brush the teeth. It is important to thoroughly brush all exposed surfaces of the teeth in order to properly remove plaque, stains, and food debris from the teeth.

The present invention is a contour-adjustable toothbrush that does not require removal from the user's mouth during brushing. The present invention is able to bend, contract, and otherwise conform to the user's teeth during brushing. Additionally, the present invention provides a more thorough brushing experience for all exposed surfaces of the user's teeth.

DETAIL DESCRIPTIONS OF THE INVENTION

Figure 1:
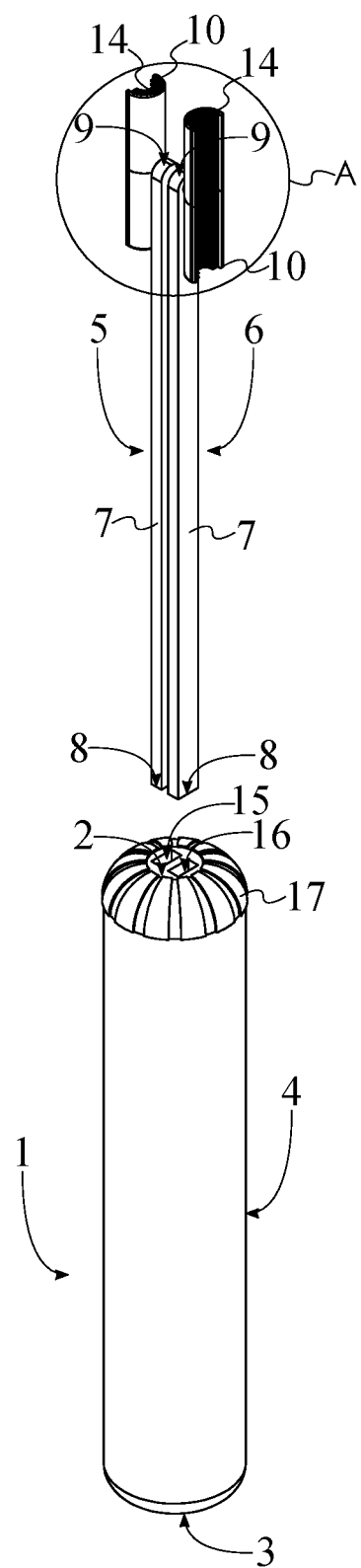
FIG. 1 is an exploded perspective view of the present invention.

All illustrations of the drawings are for the purpose of describing selected versions of the present invention and are not intended to limit the scope of the present invention.

The present invention is a contour-adjustable toothbrush that conforms to the contour of the user's teeth. The present invention is shown in FIGS. 1-6 and comprises a housing handle 1, a first brushing assembly 5, and a second brushing assembly 6.

The housing handle 1 is the portion of the present invention that is grasped by the user's hand while brushing the teeth. The housing handle 1 additionally serves as a mounting point for the first brushing assembly 5 and the second brushing assembly 6. The housing handle 1 comprises a first end 2, a second end 3, and a lateral portion 4. The first end 2 and the second end 3 are opposing ends of the housing handle 1 while the lateral portion 4 forms a sidewall that allows the user to easily grasp and maneuver the present invention. The lateral portion 4 is connected in between the first end 2 and the second end 3 and preferably forms a cylindrical extrusion that may be grasped by the user.

The first brushing assembly 5 and the second brushing assembly 6 are utilized to thoroughly brush the user's upper teeth and lower teeth simultaneously. The first brushing assembly 5 and the second brushing assembly 6 each comprise a connecting member 7, a flexible brush head 10, and a plurality of bristles 14. The connecting member 7 is an intermediary extrusion that joins the flexible brush head 10 to the housing handle 1. A proximal end 8 of the connecting member 7 is slidably engaged into the first end 2. This enables the user to adjust the positioning of the flexible brush head 10 relative to the first end 2 by sliding the connecting member 7 into or out of the first end 2. A distal end 9 of the connecting member 7 is connected onto a convex surface 11 of the flexible brush head 10. The flexible brush head 10 is thus positioned away from the first end 2 and the present invention is sized similarly to a conventional toothbrush. In some embodiments of the present invention, the flexible brush head 10 may be removably connected to the distal end 9, enabling replacement of the flexible brush head 10 as needed.

Figure 2:
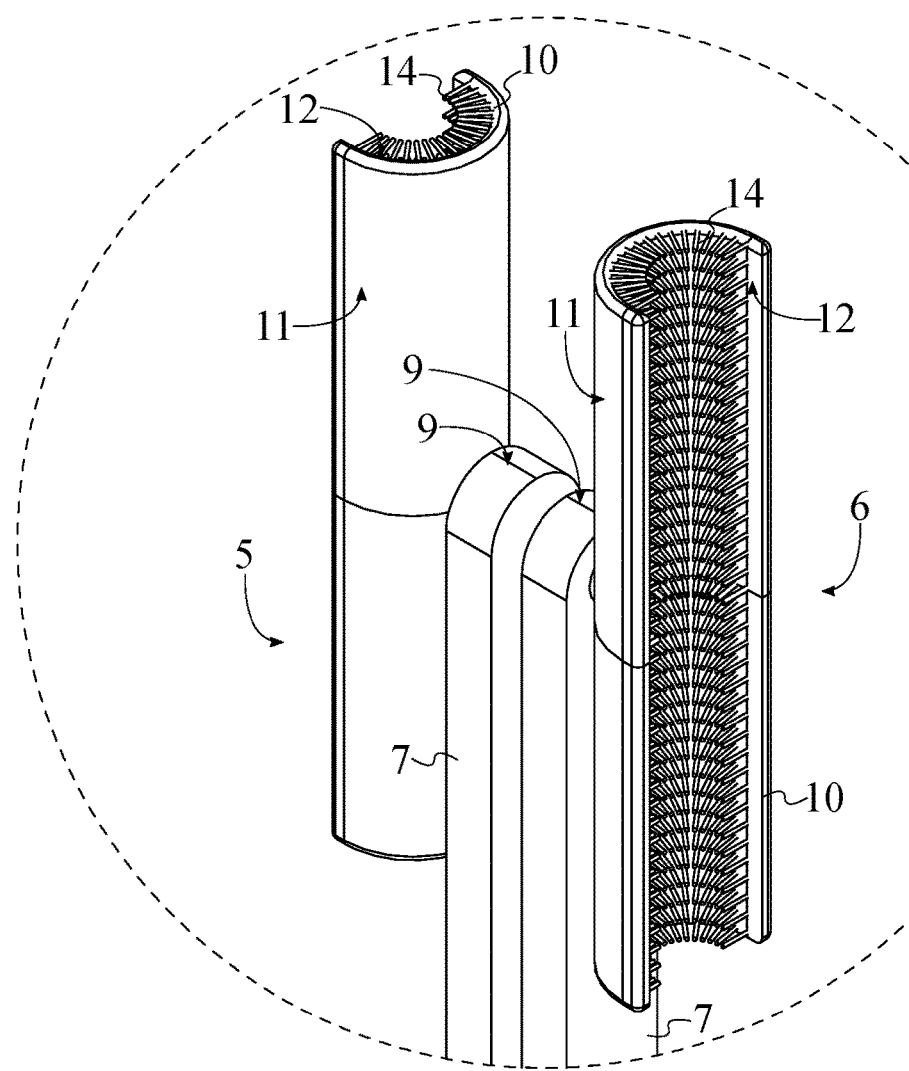
FIG. 2 is a detail view of the present invention taken from circle A of FIG. 1.
Figure 7:
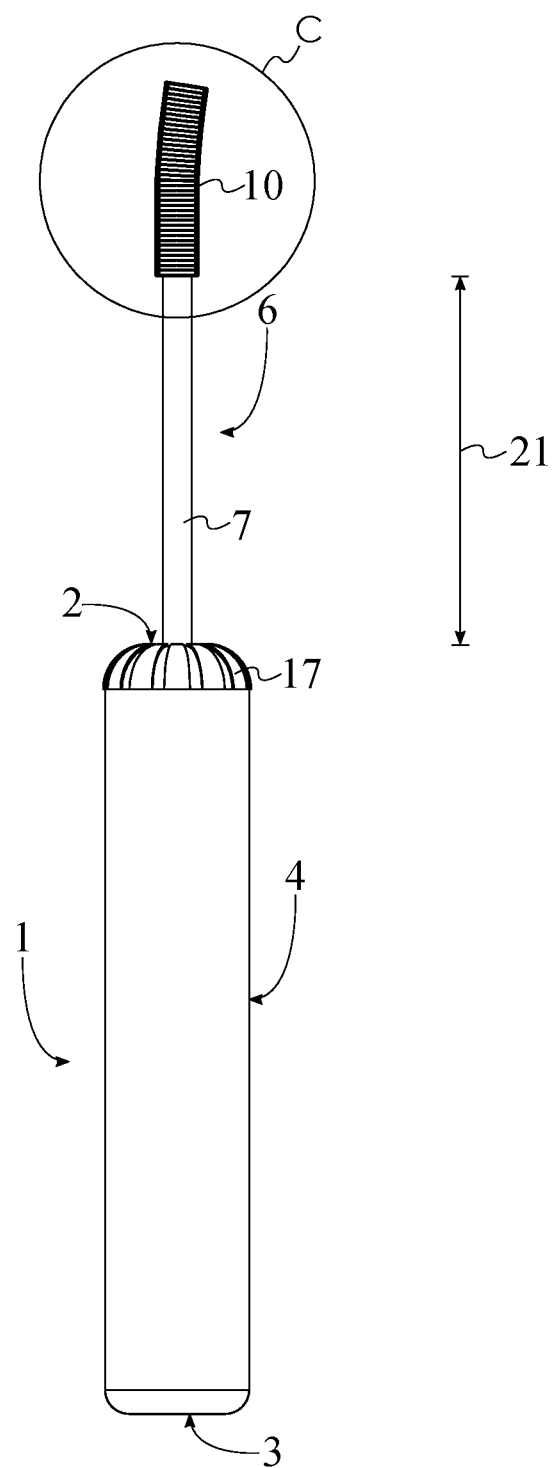
FIG. 7 is a front view of the present invention demonstrating flexibility of the flexible brush head.
Figure 8:
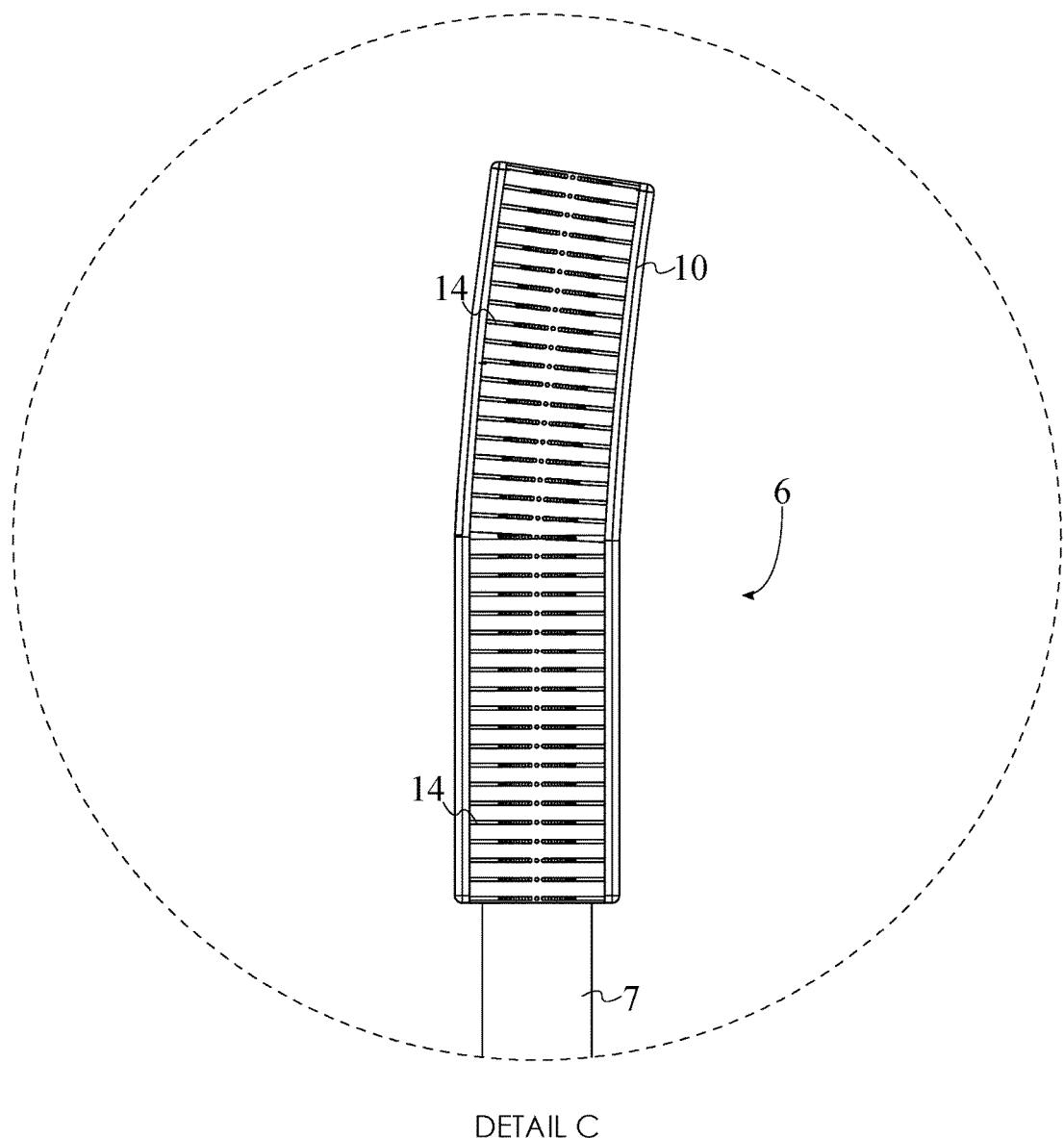
FIG. 8 is a detail view of the present invention taken from circle C of FIG. 7.

With reference to FIG. 2, the plurality of bristles 14 and the flexible brush head 10 are placed into contact with the user's teeth during brushing. The flexible brush head 10 is able to conform to the unique contour of the user's teeth. More specifically, the flexible brush head 10 is able to bend, contract, and otherwise conform to the contour of the user's teeth. Additionally, the flexible brush head 10 is able to conform to the arrangement of the user's teeth. As a result, the flexible brush head 10 is able to accommodate the curved arrangement of the user's teeth on the jaws. The flexible brush head 10 is shown in a non-curved configuration in FIG. 5 and FIG. 6. An example of the flexible brush head 10 in a curved configuration is shown in FIG. 7 and FIG. 8.

Figure 4:
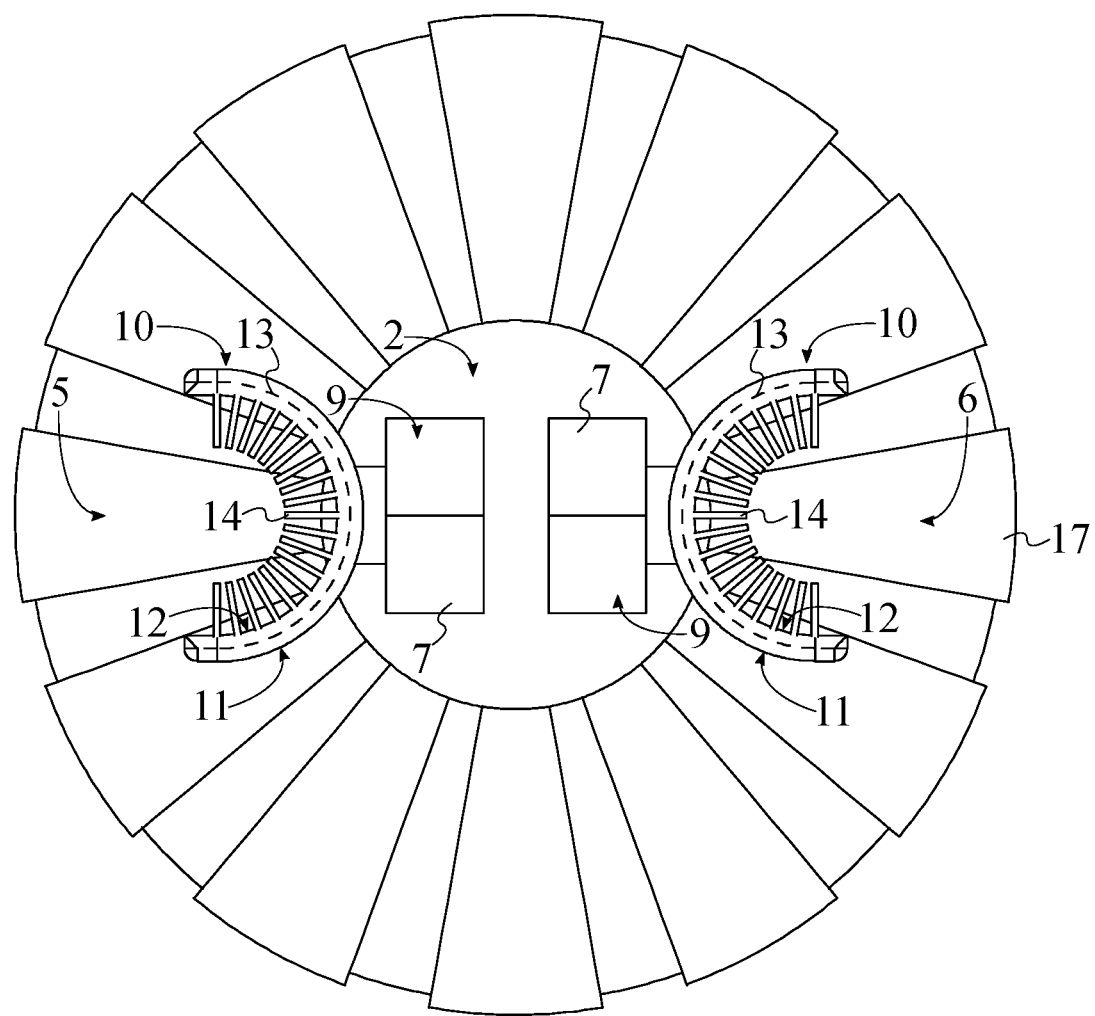
FIG. 4 is a top view of the present invention.

In the preferred embodiment of the present invention, a cross-section 13 of the flexible brush head 10 is semicircular as shown in FIG. 4. This enables the flexible brush head 10 to cover all exposed surfaces of the user's teeth during brushing. The plurality of bristles 14 is evenly distributed along a concave surface 12 of the flexible brush head 10. The plurality of bristles 14 is thus positioned in a manner such that the plurality of bristles 14 is able to come into contact with all exposed surfaces of the user's teeth. In the preferred embodiment of the present invention, the plurality of bristles 14 is oriented toward each other in order to provide thorough coverage of the user's teeth by the plurality of bristles 14 on the concave surface 12.

As shown in FIG. 1, FIG. 2, and FIG. 4, the concave surface 12 of the first brushing assembly 5 is oriented away from the concave surface 12 of the second brushing assembly 6. As a result, the first brushing assembly 5 is able to come into contact with the user's upper teeth while the second brushing assembly 6 is able to come into contact with the user's lower teeth, or vice versa. In the preferred embodiment of the present invention, the flexible brush head 10 is rotatably connected to the distal end 9. This enables the connecting member 7 to rotate about the flexible brush head 10. By extension, the housing handle 1 is able to rotate about the flexible brush head 10 as well. This eliminates the need to remove the present invention from the mouth when brushing from the left side of the mouth to the right side of the mouth and vice versa. The user may simply flip the housing handle 1 by rotating the housing handle 1 and the connecting member 7 about the flexible brush head 10 when transitioning from one side of the mouth to the other side of the mouth.

As shown in FIG. 1, the present invention further comprises a first brush slot 15 and a second brush slot 16. The first brush slot 15 and the second brush slot 16 house the connecting member 7 of the first brushing assembly 5 and the connecting member 7 of the second brushing assembly 6, respectively. The first brush slot 15 and the second brush slot 16 enable adjustment in terms of the length of the present invention. The first brush slot 15 and the second brush slot 16 traverse into the housing handle 1 from the first end 2. The first brush slot 15 and the second brush slot 16 thus provide an elongated channel within the housing handle 1 that is accessible from the first end 2. In the preferred embodiment of the present invention, the connecting member 7 of the first brushing assembly 5 and the connecting member 7 of the second brushing assembly 6 are oriented parallel to each other. The connecting member 7 of the first brushing assembly 5 and the connecting member 7 of the second brushing assembly 6 are thus aligned side-by-side with each other.

Figure 3:
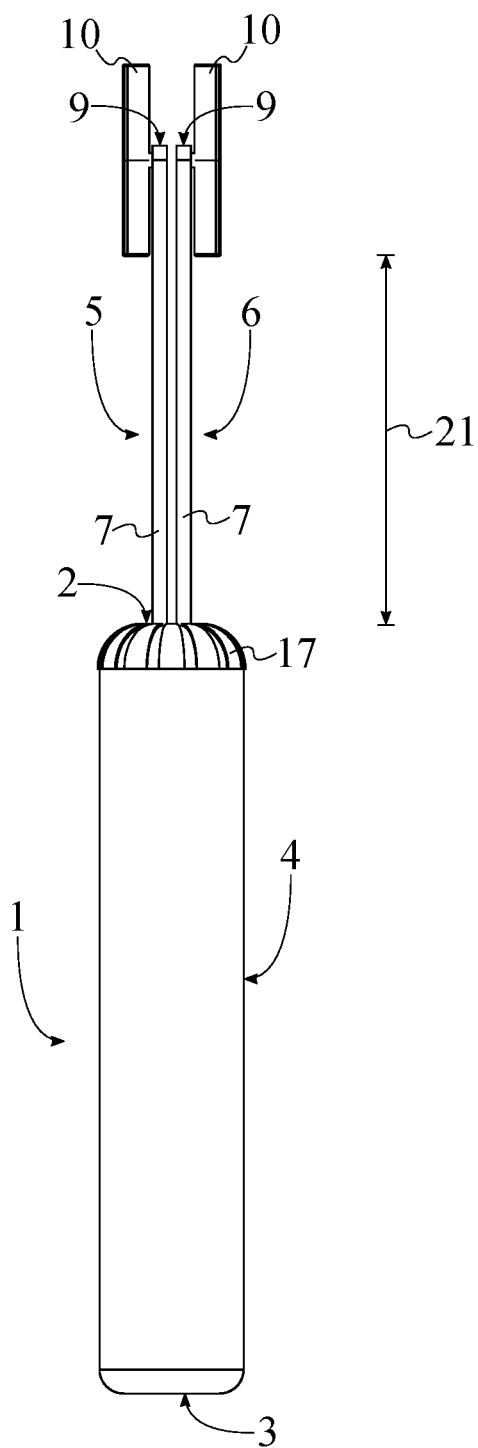
FIG. 3 is a front view of the present invention.
Figure 5:
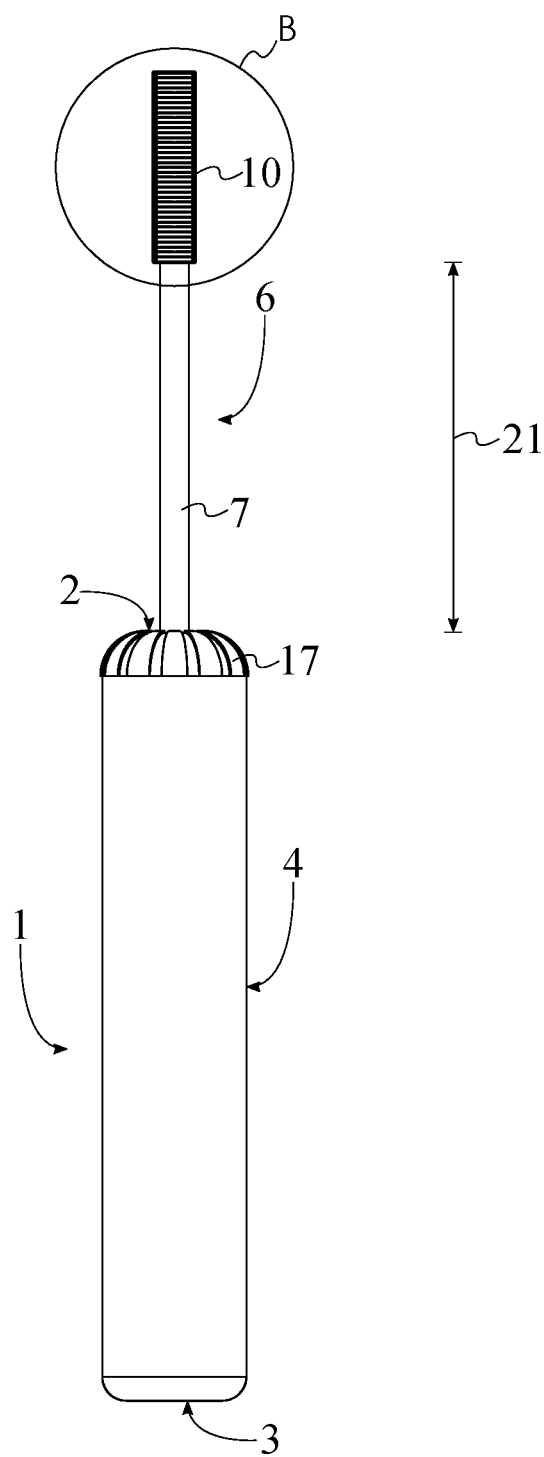
FIG. 5 is a right side view of the present invention.
Figure 6:
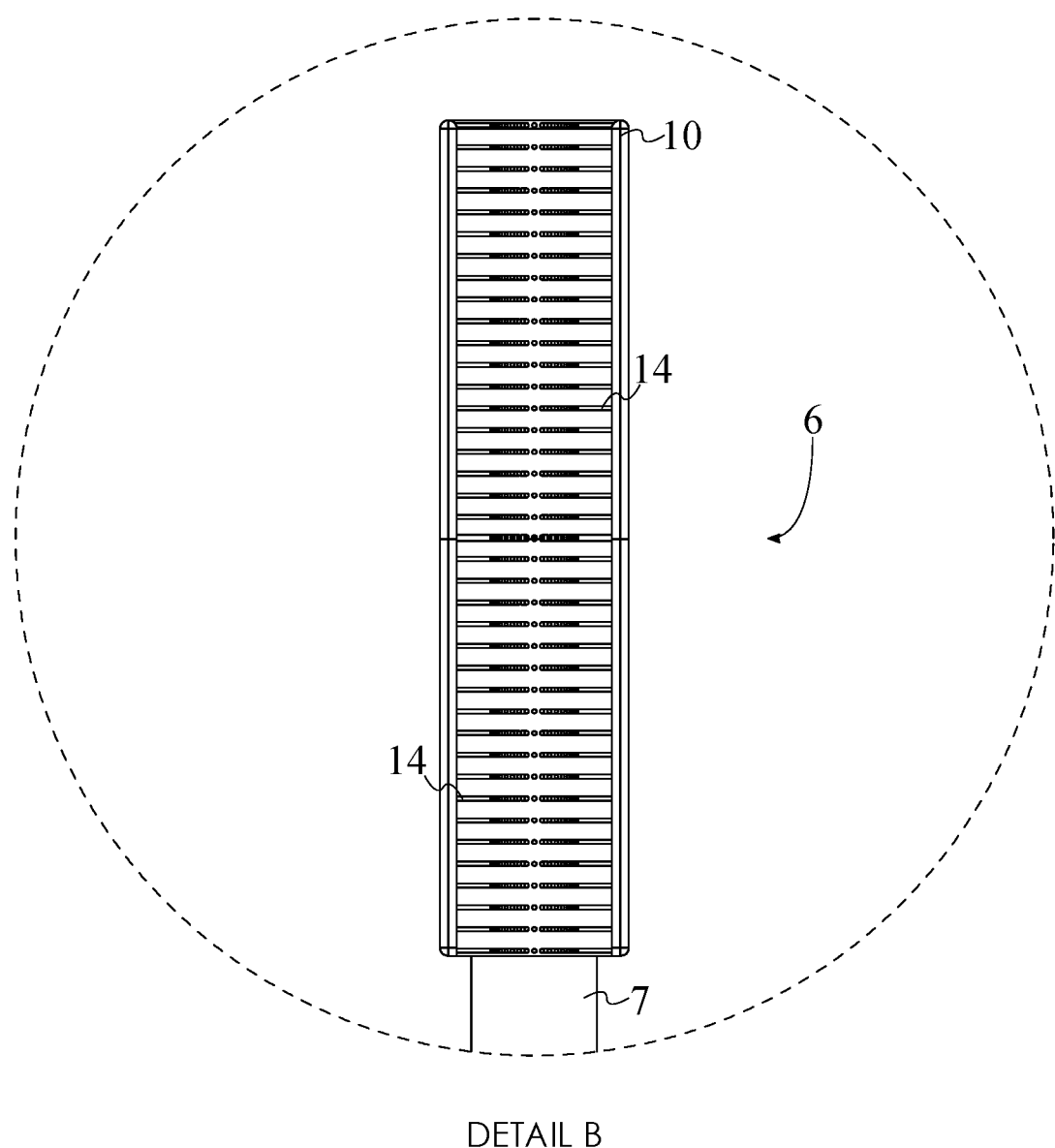
FIG. 6 is a detail view of the present invention taken from circle B of FIG. 5.

As seen in FIG. 3, FIG. 5, and FIG. 7, the flexible brush head 10 is offset from the first end 2 by an adjustable length 21. The user is able to slide the connecting member 7 into or out of the housing handle 1 in order to adjust the length of the present invention. This reduces the likelihood of gagging and impalement when brushing the teeth utilizing the present invention as the user is able to reduce the size of the present invention. The connecting member 7 of the first brushing assembly 5 is slidably engaged into the first brush slot 15 while the connecting member 7 of the second brushing assembly 6 is slidably engaged into the second brush slot 16. The connecting member 7 of the first brushing assembly 5 and the connecting member 7 of the second brushing assembly 6 are adjustable independently of each other. The present invention may thus be adjusted in order to accommodate conditions such as overbite and underbite. The present invention further comprises a brush locking mechanism 17 that secures the connecting member 7 in place within the housing handle 1 following adjustment. The brush locking mechanism 17 is mechanically integrated between the housing handle 1 and the connecting member 7. The user may thus engage the brush locking mechanism 17 after independently adjusting the connecting member 7 of the first brushing assembly 5 and the connecting member 7 of the second brushing assembly 6. The present invention is not limited with respect to a specific mechanism for the brush locking mechanism 17. An example mechanism is a rotatable adjustment knob that is able to adjust the amount of friction holding the connecting member 7 of the first brushing assembly 5 and the connecting member 7 of the second brushing assembly 6 in place within the first brush slot 15 and the second brush slot 16.

Figure 9:
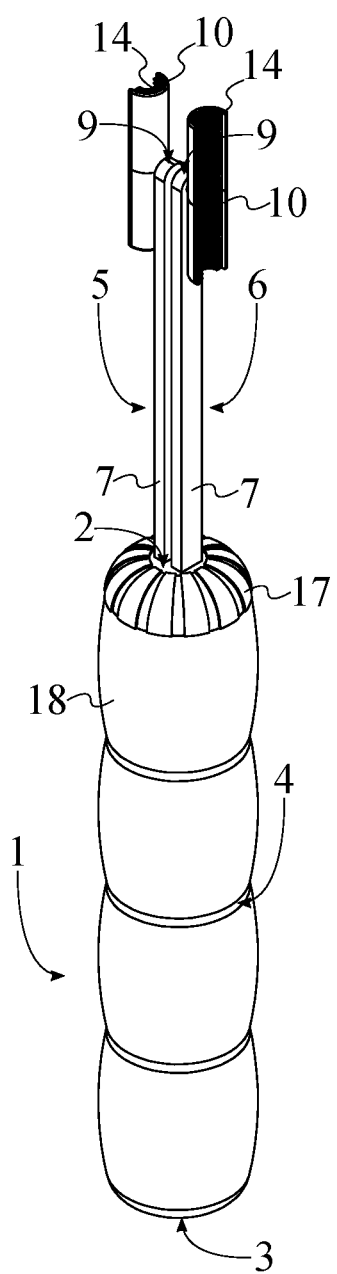
FIG. 9 is a perspective view of the present invention with the at least one gripping feature as a rubberized coating.
Figure 10:
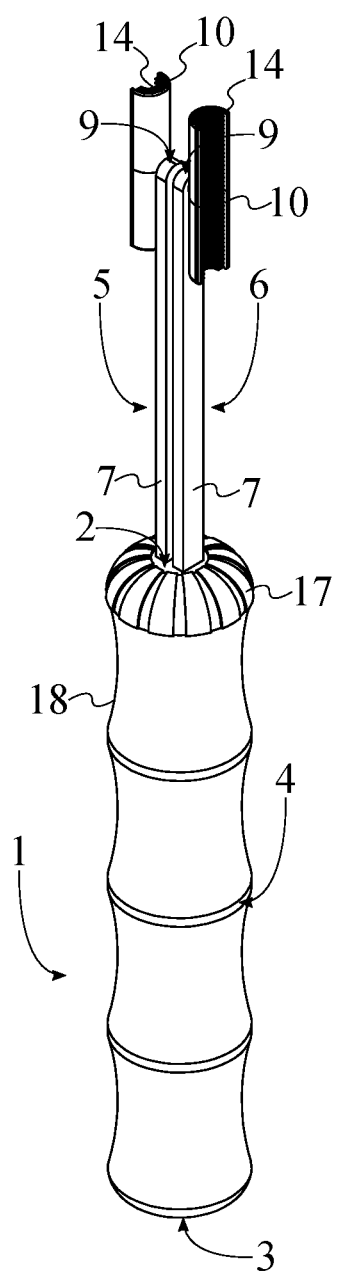
FIG. 10 is a perspective view of the present invention with the at least one gripping feature as a plurality of grooves.

In order to increase user comfort when utilizing the present invention, the present invention may further comprise at least one gripping feature 18. The at least one gripping feature 18 is integrated into and about the lateral portion 4 as the lateral portion 4 is the region of the housing handle 1 that is grasped by the user during use of the present invention. Two examples of the at least one gripping feature 18 are shown in FIG. 9 and FIG. 10. With reference to FIG. 9, the at least one gripping feature 18 is a rubberized coating. In this example, the at least one gripping feature 18 increases the grip of the user's hand on the housing handle 1 and minimizes slippage during brushing. With reference to FIG. 10, the at least one gripping feature 18 is a plurality of grooves. In this example, the at least one gripping feature 18 improves retention of the user's fingers on the housing handle 1 as well as the ergonomics of the housing handle 1 during brushing.

Figure 11:
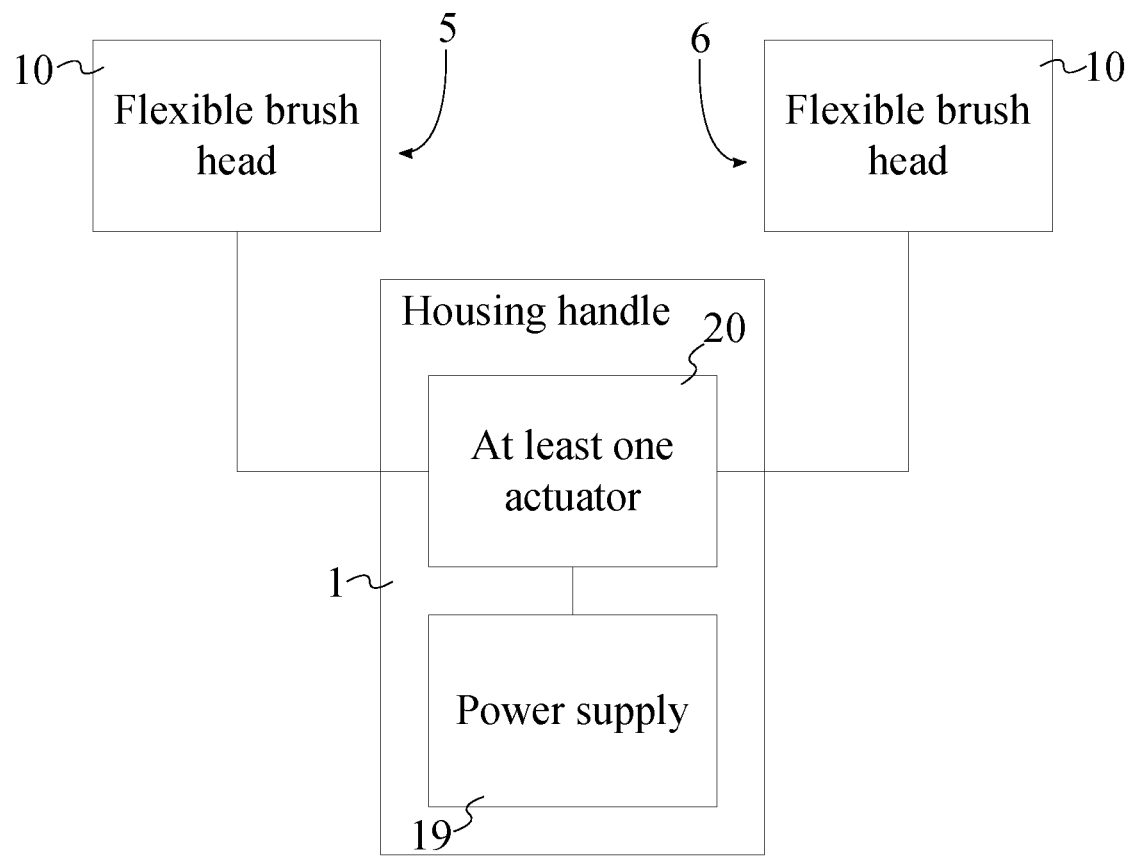
FIG. 11 is a diagram depicting electronic and electrical connections of the present invention.

The present invention thus far has been described as a manually operated toothbrush. However, various embodiments of the present invention may include electric capabilities and functionality. With reference to FIG. 11, the present invention may further comprise a power supply 19 and at least one actuator 20. The power supply 19 provides electrical power to the at least one actuator 20 while the at least one actuator 20 is able to vibrate or otherwise actuate the flexible brush head 10, similar to a conventional electric toothbrush. The power supply 19 and the at least one actuator 20 are enclosed within the housing handle 1 in order to protect the power supply 19 and the at least one actuator 20 from water and other potentially damaging elements. The power supply 19 may be a battery that is replaceable upon depletion. The power supply 19 is electrically connected to the at least one actuator 20, allowing electrical power to be provided to the at least one actuator 20 by the power supply 19. The at least one actuator 20 is mechanically coupled to the flexible brush head 10 of the first brushing assembly 5 and the flexible brush head 10 of the second brushing assembly 6. The at least one actuator 20 is thus able to vibrate or otherwise actuate the flexible brush head 10 of the first brushing assembly 5 and the flexible brush head 10 of the second brushing assembly 6. The at least one actuator 20 may be toggled on and off via a switch.

Although the present invention has been explained in relation to its preferred embodiment, it is understood that many other possible modifications and variations can be made without departing from the spirit and scope of the present invention as hereinafter claimed.

What is claimed is:

1. A contour-adjustable toothbrush comprising:
   a housing handle;
   a first brushing assembly;
   a second brushing assembly;
   the housing handle comprising a first end, a second end and a lateral portion;
   the first brushing assembly and the second brushing assembly each comprising an elongated connecting member, a flexible brush head and a plurality of bristles;
   the flexible brush head comprising a curved configuration;
   the curved configuration being formed in response to the flexible brush head being bent;
   the lateral portion being connected in between the first end and the second end;
   the elongated connecting member comprising a proximal end and a distal end opposite to each other along an extension line;
   the proximal end being slidably engaged into the first end;
   the flexible brush head comprising a convex surface and a concave surface opposite to each other;
   the distal end being connected onto the convex surface;

the flexible brush head being rotatably connected to the distal end around a rotation axis;
the extension line and the rotation axis being perpendicular to each other;
the plurality of bristles being evenly distributed along the concave surface;
the concave surface of the first brushing assembly being oriented away from the concave surface of the second brushing assembly;
a gripping feature;
the gripping feature being integrated into and about the lateral portion; and
the gripping feature comprising a plurality of grooves.

2. The contour-adjustable toothbrush as claimed in claim 1 comprising:
a cross-section of the flexible brush head being semicircular.

3. The contour-adjustable toothbrush as claimed in claim 1 comprising:
the flexible brush head being offset from the first end by an adjustable length.

4. The contour-adjustable toothbrush as claimed in claim 1 comprising:
a first brush slot;
a second brush slot;
the first brush slot and the second brush slot traversing into the housing handle from the first end;
the elongated connecting member of the first brushing assembly being slidably engaged into the first brush slot; and
the elongated connecting member of the second brushing assembly being slidably engaged into the second brush slot.

5. The contour-adjustable toothbrush as claimed in claim 1 comprising:
the elongated connecting member of the first brushing assembly and the elongated connecting member of the second brushing assembly being oriented parallel to each other.

6. The contour-adjustable toothbrush as claimed in claim 1 comprising:
the flexible brush head being removably connected to the distal end.

7. The contour-adjustable toothbrush as claimed in claim 1 comprising:
a brush locking mechanism; and
the brush locking mechanism being mechanically integrated between the housing handle and the elongated connecting member.

8. The contour-adjustable toothbrush as claimed in claim 1 comprising:
the plurality of bristles being oriented toward each other.

9. The contour-adjustable toothbrush as claimed in claim 1 comprising:
the gripping feature comprising a rubberized coating.

10. The contour-adjustable toothbrush as claimed in claim 1 comprising:
a power supply;
at least one actuator;
the power supply and the at least one actuator being enclosed within the housing handle;
the power supply being electrically connected to the at least one actuator; and
the at least one actuator being mechanically coupled to the flexible brush head of the first brushing assembly and the flexible brush head of the second brushing assembly.

* * * * *